United States Patent
Malaney et al.

(10) Patent No.: US 6,377,853 B1
(45) Date of Patent: Apr. 23, 2002

(54) IMPLANTABLE ELECTRO-ACUPUNCTURE DEVICE

(75) Inventors: James Malaney, Iowa City, IA (US); Randy Nelson, Pine Springs, MN (US)

(73) Assignee: Urosurge, Inc., Coralville, IA (US)

( * ) Notice: Subject to any disclaimer, the term of this patent is extended or adjusted under 35 U.S.C. 154(b) by 0 days.

(21) Appl. No.: 09/457,217

(22) Filed: Dec. 9, 1999

(51) Int. Cl.⁷ .................................................. A61N 1/05
(52) U.S. Cl. ............................................................ 607/61
(58) Field of Search ........................ 607/1–156; 600/377

(56) References Cited

U.S. PATENT DOCUMENTS

| | | |
|---|---|---|
| 3,357,434 A | 12/1967 | Abell ........................ 128/419 |
| 3,724,467 A | 4/1973 | Avery et al. ................. 128/418 |
| 4,262,672 A | 4/1981 | Kief ....................... 128/329 A |
| 4,577,635 A | 3/1986 | Meredith ..................... 128/642 |
| 4,765,310 A | 8/1988 | Deagle et al. ................ 128/1.5 |
| 5,094,242 A | 3/1992 | Gleason et al. .............. 128/642 |
| 5,733,322 A | * | 3/1998 Starkebaum |

* cited by examiner

Primary Examiner—Scott M. Getzow
(74) Attorney, Agent, or Firm—Dorsey & Whitney LLP; Scott D. Rothenberger

(57) ABSTRACT

Improved implantable devices for electro-acupuncture are described. The devices include a flexible conductor electrode, an anchor fixation for preventing motion of the device in tissue after implantation, and/or a sealed, liquid-impermeable housing.

27 Claims, 3 Drawing Sheets

IMPLANTABLE ELECTRO-ACUPUNCTURE DEVICE

BACKGROUND OF THE INVENTION

The technical field of this invention is electro-stimulation of tissue in vivo for therapeutic purposes.

The use of acupuncture to relieve pain and produce other therapeutic results has been common in certain cultures for many years, but only recently has this practice gained a significant following in the United States. The increased recognition of the utility of acupuncture in medicine has led to new forms of acupuncture therapy such as electro-acupuncture, in which the acupuncture needle is connected to a power source to deliver an electric current to an acupuncture point. Electro-acupuncture has the potential to combine the benefits of conventional acupuncture with the advantages of electrical nerve stimulation.

Such new acupuncture practices require the development of devices and methods suitable for safe, reliable delivery of an electric current via an implantable needle. Implantable electro-acupuncture devices have been described (e.g., U.S. Pat. Nos. 5,094,242 and 5,211,175 to Gleason et al.). However, although these devices solve many of the problems associated with prior art devices for electrical stimulation, they may not be suitable for long-term implantation due to the possibility that their needles will move or shift within tissue, thereby removing the needles from the desired site of electrical stimulation over time. Moreover, the relatively inflexible needle of previous devices may not be able to accommodate a full range of tissue motion, with the accompanying risk of metal fatigue and eventual fracture of the needle or other device components, and possible damage to surrounding tissue. Furthermore, prior art devices often fail due to corrosion or short-circuits that occur as a result of the infiltration of body fluids into the device over time.

SUMMARY OF THE INVENTION

Improved implantable devices for electro-acupuncture and electrical stimulation having one or more flexible electrodes for delivering an electric impulse to tissue are herein disclosed. These devices may also include anchoring mechanisms for preventing motion of the conductor electrode relative to tissue, and/or may have sealed, liquid-tight housings. The implantable devices of the invention are suitable for implantation in a patient's tissue for extended time periods.

In one aspect, the invention provides an implantable nerve stimulation device which includes a housing which defines a cavity, a source of electrical current disposed within the cavity, a first electrode for applying an electric current to tissue, and a second electrode in electrical connection with the source of electric current for receiving the electric current after the current has passed through tissue. The second electrode is in electrical communication with the source of electric current, and, preferably, is secured to the housing at a proximal end of the first electrode. The first electrode can be a flexible conductor, having a distal end adapted for conducting an electric impulse to the tissue.

In another aspect, the invention provides an implantable nerve stimulation device which includes a housing which defines a cavity, a source of electrical current disposed within the cavity, a first electrode for applying an electric current to tissue, and a second electrode in electrical connection with the source of electric current for receiving the electric current after the current has passed through tissue. The second electrode is in electrical communication with the source of electric current, has a distal end for applying an electrical current to tissue, and is secured to the housing at a proximal end of the first electrode. The first electrode further includes an anchor for fixing the distal end of the first electrode relative to the tissue and for resisting movement within the tissue.

In still another aspect, the invention relates to an implantable nerve stimulation device which includes a housing which defines a cavity, a source of electrical current disposed within the cavity, a first electrode for applying an electric current to tissue, and a second electrode in electrical connection with the source of electric current for receiving the electric current after the current has passed through tissue. The second electrode is in electrical communication with the source of electric current, and is secured to the housing at a proximal end of the first electrode. The housing is hermetically sealed to prevent ingress of body fluids into the cavity. The hermetically sealed housing may, for example, consist in part of a ceramic lid that allows high frequency energy to pass without being attenuated as with a comparable metal housing.

The implantable nerve stimulation device may also include a protective member, such as a strain relief boot, to protect the interface between the housing and the conductor, and/or may include a securing mechanism to suture a portion of the device to tissue in order to deter or prevent movement of the device from its site of implantation.

In any of the above aspects of the invention, an internal power source may act as the source of electrical current, wherein the internal power source can be activated and deactivated remotely.

DETAILED DESCRIPTION OF THE INVENTION

This invention relates to the field of electro-acupuncture devices, and particularly to implantable devices for electrical stimulation of nerves.

Figure 1:
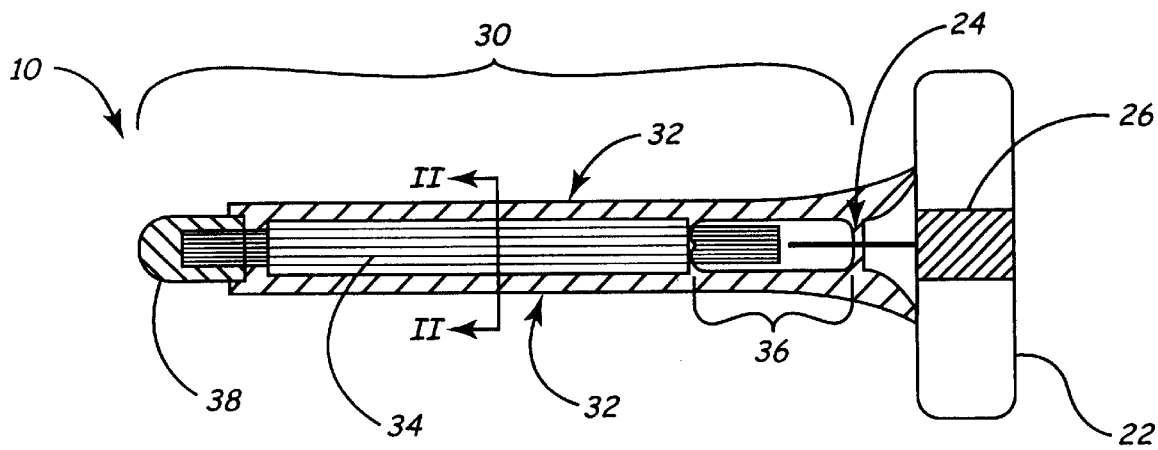
FIG. 1 is a longitudinal cross-sectional, side view of an electro-acupuncture device of the invention.
Figure 1A:
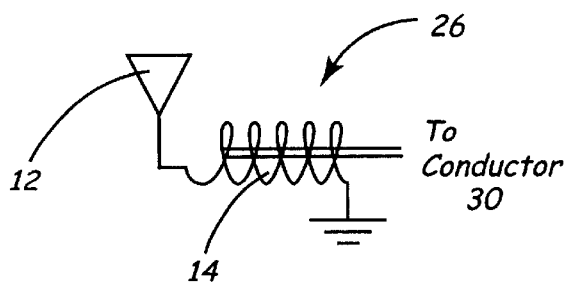
FIG. 1A is a circuit diagram for an illustrative electrical source for use in the invention.

In FIG. 1, an implantable electro-acupuncture device 10 is shown including a housing 22, and conductor 30 for electrically stimulating tissue. The conductor 30 passes through an opening 24 in the housing 22 using either a lateral or tangential interface method. Inside the housing 22 is a voltage or current source 26 for providing an electrical stimulus to the conductor 30. As shown schematically in FIG. 1A, source 26 can be a receiver 12 coupled to an inductive coil 14 in electrical connection with the conductor electrode 30. For further details regarding the source, see, for example, U.S. Pat. No. 5,094,242. In this embodiment, the receiver can receive radio-frequency signals from an external antenna connected to an external generator-transmitter; the inductive coil converts the received signal to an electrical impulse which is supplied to the tissue through the conductor 30. The signals provided by the external generator-transmitter can determine the pulse width, the sequence and interval of pulses, and the power of pulses which are provided by electrical source 26 and thus provided to the tissue of the patient. Alternatively, source 26 can include a battery and electrical circuitry for providing a current to the conductor. In this embodiment, the source 26 can include additional circuitry for providing electrical impulses; the circuitry can be configured to permit a variety of pulse widths, pulse trains, power levels, and the like, depending upon the particular therapeutic requirements of the patient. In this embodiment, the parameters of the electrical pulses to be provided by the device 10 to the patient's tissue can be pre-set prior to implantation of the device; or the source 26 can alternatively be provided with a controller for re-setting the parameters after implantation of the device. For example, the controller can further include a receiver which can receive commands from an external antenna and be reprogrammed in response to the received commands to alter the characteristics of the electrical pulses.

The housing 22 is electrically coupled to one terminal of the source 26. In a preferred embodiment, housing 22 is constructed of an electrically conducting material such as titanium or stainless steel, as described in more detail below. Alternatively, the housing 22 can be constructed of a non-conducting (insulating) material, provided that an electrode is provided to complete the electrical circuit between the conductor 30 and one terminal of the source 26. For example, housing 22 can be constructed from an insulating material such as a biocompatible plastic or ceramic, with a ring electrode (not shown) embedded in and extending through the shell and providing an electrical contact with tissue and with electric voltage or current source 26.

To prevent short circuits, conductor 30 is generally electrically insulated from contact with housing 22. If housing 22 is constructed of an electrically conducting material, electrical insulation between the housing 22 and conductor 30 can be provided by coating the conductor with an insulating material, such as Teflon, or by inserting the conductor 30 through a plug of a suitable dielectric material to provide insulation between the conductor and the housing. In preferred embodiments, the conductor 30 is coated or covered with a suitable biocompatible insulating layer 32 along a substantial portion of the longitudinal extent of the conductor 30, leaving only the distal tip 38 of the conductor 30 in electrical connection with the tissue when the device 10 is implanted. The insulating layer 32 can be a layer or combination of layers of, e.g., silicone, polyurethane or poly(tetrafluoroethylene) (PTFE), or any other biocompatible electrically insulator known to those of skill in the art.

Figure 2:
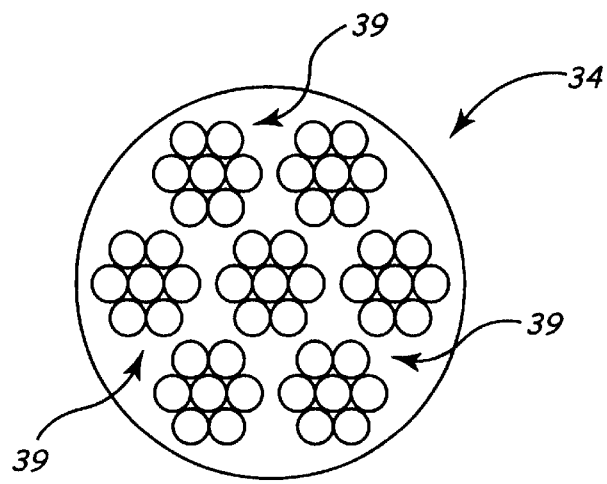
FIG. 2 is a cross-sectional, end view of a conductor element of the device, viewed along the direction of arrows II—II of FIG. 1.

The conductor 30 is preferably constructed of materials which permit the conductor 30 to flex or deform generally according to the movement of tissues which surround the implantable device 10 when the device is surgically implanted. Thus, the conductor 30 is preferably constructed of an electrically conducting cable or coil. The material selected for construction of the conductor 30 should have an electrical conductivity sufficient to permit the electrical impulses provided by electrical source 26 to pass through the conductor 30 without unwanted resistive heating of the conductor 30 or the surrounding tissue. In one preferred embodiment, the conductor 30 is configured as a multi-stranded cable, as shown in cross-sectional view in FIG. 2. In the embodiment shown in FIG. 2, the cable 34 includes smaller multi-stranded cables 39 which can be twisted together to form cable 34. Such a stranded cable can provide sufficient electrical conductivity while maintaining flexibility of the conductor 30. Other flexible conductive cables which are suitable for use in the present invention will be apparent to the ordinarily skilled artisan.

Returning to the description of FIG. 1, the conductor 30 can be formed of a unitary conductor cable, or conductor 30 can be formed of conductive sections which are secured to each other in electrical connection. Thus, for example, in the embodiment shown in FIG. 1, the conductor 30 comprises a conductive cable 34, which is secured to the housing 22 through a crimp connection 36. Both the cable portion 34 and the crimp 36 are covered with insulating layer 32. The conductor 30 also includes an electrically conductive tip portion 38, which is crimped to the cable portion 34. Tip section 38 contacts the tissue of the patient and supplies electrical impulses from electrical source 26 to the tissue. Tip section 38 may be a variety of shapes including, but not limited to, pointed and substantially rounded.

Figure 3:
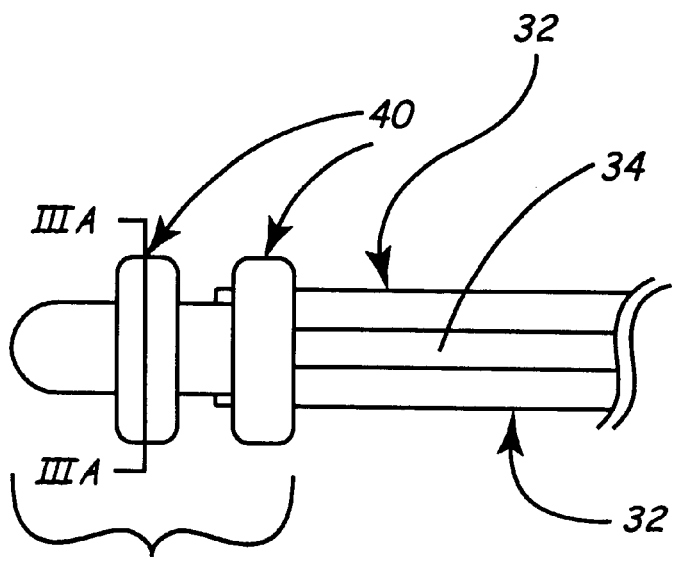
FIG. 3 is a longitudinal, cross-sectional, side view of an alternate embodiment of the device of FIG. 1 with an anchor disposed at the distal portion of the device.
Figure 3A:
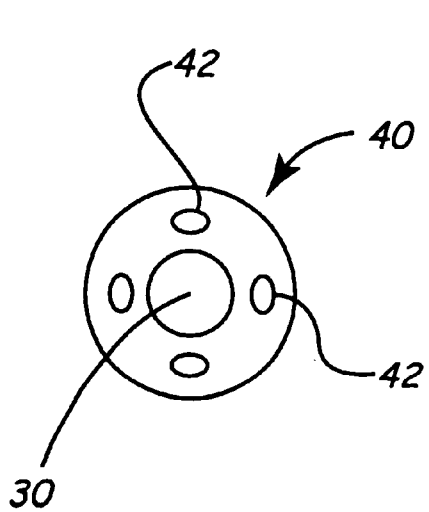
FIG. 3A is a front view of the anchor of FIG. 3.

In preferred embodiments, the conductor 30 is provided with an anchor to reduce or eliminate relative motion between the distal (non-insulated) portion of the conductor (e.g., tip 38) and the patient's tissue. By reducing motion of the conductor tip with respect to tissue, the possibility that the conductor may cause tissue scarring or damage can be decreased. Moreover, by reducing the probability that the tip will move away from the desired target site or nerve, the probability that the device will, over time, move and thereby fail to provide an electrical impulse to the correct location in tissue, is reduced. Motion of the conductor tip after implantation can be reduced by providing the conductor tip with an anchor for engaging tissue. For example, FIG. 3 depicts a passive fixation anchor 40, which has the form of a ridge or flange which extends around all or part of the distal portion 41 of the conductor 30. The anchor 40 can engage and become entrapped in tissue, and resist movement through the tissue, thereby decreasing motion of the conductor 30 in the tissue. However, in a preferred embodiment, the anchor is configured, in size or shape, to allow removal of the conductor 30 from tissue, e.g., to permit surgical removal of the device 10 when therapy is discontinued. The anchoring ridge or flange can be integrally formed with a portion of the conductor 30 or the insulation layer 32 (e.g., the anchor can be formed of an insulating polymer), or the anchor can be a separate portion which is fixed to the conductor, e.g., by cementing or welding. As shown in FIG. 3A, the anchor can include one or more bores 42 that facilitate the placement and/or removal of the anchor. When the device 10 is surgically implanted within the patient's tissue, the anchor can be placed at a desired location within the tissue to ensure proper placement of the conductor.

Figure 4:
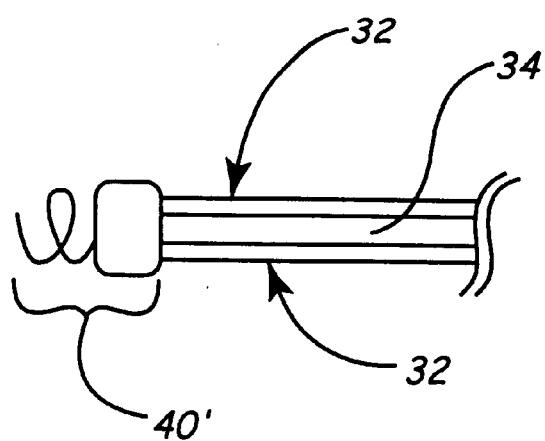
FIG. 4 is a longitudinal, cross-sectional, side view of another alternate embodiment of the device of FIG. 1 with an alternate anchor disposed at the distal portion of the device.

An alternative fixation anchor is shown in FIG. 4. In this embodiment, the anchor 40' has the form of a helical tissue-engaging member, such as a wire or coil, which can be turned or rotated to engage the tissue. In this embodiment, placement of the device 10 (e.g., by a surgeon) is accomplished by siting the conductor 30 at the desired location and turning or rotating the helical member 40' (which can rotate with the conductor or can be rotatably secured to the conductor to permit separate rotation of the helical member while the conductor remains stationary) until the helical member engages tissue to stabilize the conductor tip against motion relative to the tissue. To facilitate placement by the physician, the helical member can be covered or otherwise prevented from engaging tissue during the initial implantation of the device 10; the cover can be removed to permit the helical member to engage tissue once the implant 10 is positioned in the desired location. In a preferred embodiment, the helical member is configured, in size or shape, to allow removal of the conductor 30 from tissue, e.g., to permit surgical removal of the device 10 when therapy is discontinued.

Referring again to the embodiment of FIG. 1, the housing 22 of the device 10 contains the electrical circuitry and components necessary to provide electrical impulses to the patient's tissue, as described above. To avoid damage to the electrical components of the device, the housing 22 is preferably sealed to prevent liquids, such as body fluids, from contacting the interior of the housing. The housing preferably is sealed to prevent intrusion of liquids into the housing even after an extended period of implantation, e.g., after 1 month, 2 months, 3 months, 6 months, one year or longer period of implantation. As previously described, it is also preferable to construct at least a portion of the housing 22 of an electrically-conductive material, to permit the surface of the housing to serve as a counter electrode for completing an electrical circuit in combination with the conductor 30. By providing a large surface area, an electrically conductive housing serves as a large counter electrode, reducing the amount of current to which surrounding, non-target tissues are exposed.

Thus, in a preferred embodiment, the housing 22 is at least partially formed of an electrically-conductive material, and is sealed in liquid-tight sealing relation with the conductor 30. The conductive housing 22 can be formed of, e.g., titanium, biocompatiblegrade stainless steel, or other conductors which have sufficient conductivity, biocompatibility, and resistance to attack by body fluids or tissues. The housing 22 can be provided by sealing together two components of the housing (e.g., two halves of the housing), with the electronic elements sealed inside and in electrical contact with the housing. The housing components can be welded together (e.g., by laser or Tungsten inert gas welding) to provide a liquid-tight seal between the components. As previously described, the housing 22 has a pass-through opening 24 which permits electrical contact of the current source 26 with the flexible conductor 30. The opening 24 can comprise a ferrule (not shown) welded to the housing 22. The opening 24 may be covered with a suitable material, such as silicone, to prevent liquid and access and ingress and to provide mechanical strength. If the housing 22 is formed of an electrically-conductive material, the conductor 30 must be electrically insulated from the housing. This result can be achieved by providing a sealing insulator such a ceramic, glass, sapphire, non-conductive plastics, and the like.

Figure 5A:
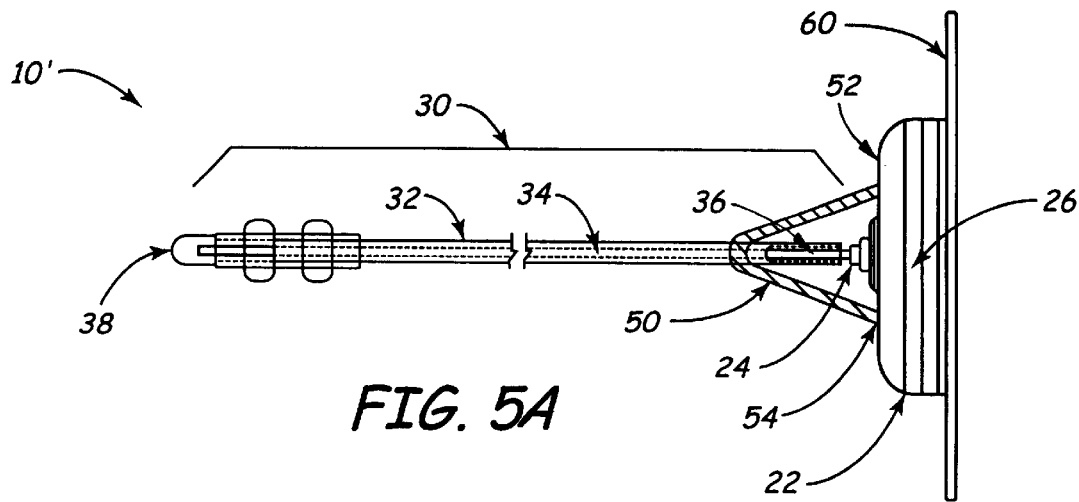
FIG. 5A is longitudinal, cross-sectional, side view of yet another alternate embodiment of the device of claim 1.
Figure 5B:
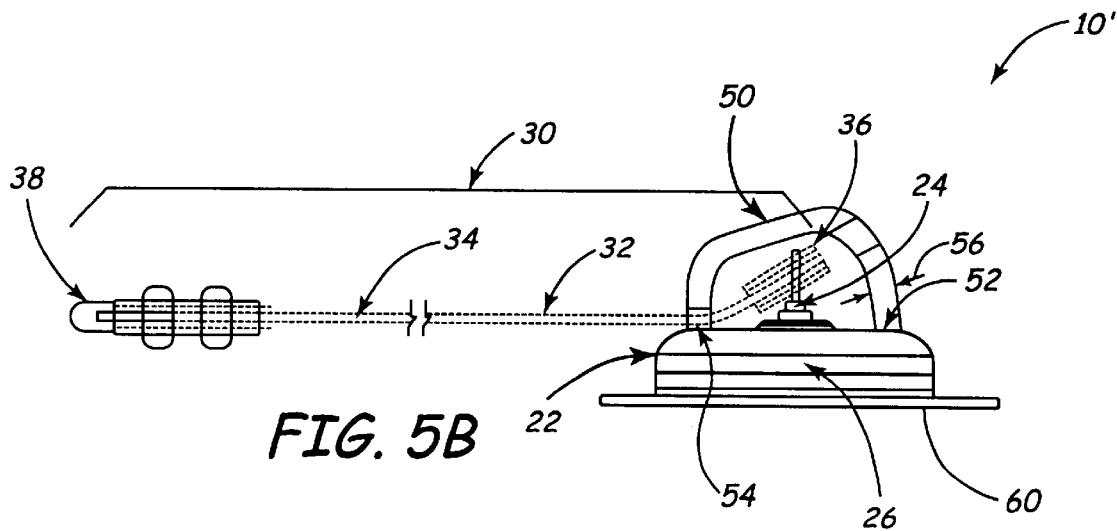
FIG. 5B is longitudinal, cross-sectional, side view of still another alternate embodiment of the device of claim 1.

Referring now to FIGS. 5A and 5B, an alternate embodiment of the implantable nerve stimulation device of FIG. 1 is shown. The device 10' of FIGS. 5A and 5B generally has identical components as described with respect to FIGS. 1 and 2, and also may utilize either of the fixation anchors described in FIGS. 3, 3A and 4. As shown in FIGS. 5A and 5B, however, the device 10' may also include a protecting member 50 to protect the interface between the housing 22 and the conductor 30, and/or a securing mechanism 60 to suture a to portion of the device 10' to a tissue site to prevent or deter movement of the device from the tissue site.

The protective member 50 is generally a strain relief boot and is positioned so as to completely enclose the interface between the conductor 30 and the housing 22. The protective member is effective to protect the areas which it encloses from damage and short circuits that could be caused by, for example, body fluids. The protective member 50 should be made of a biocompatible material. Preferably, the protective member is made out of a biocompatible, insulating material such as silicone or polyurethane.

Figure 6:
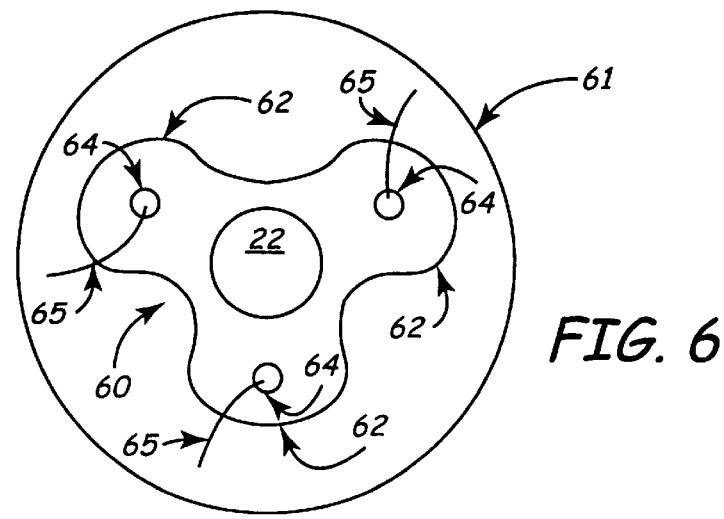
FIG. 6 is a top view of an exemplary tie-down mechanism of FIGS. 5A or 5B.

The protective member may be shaped and positioned in several ways, two of which are shown in FIGS. 5A and 5B. In each instance, however, the protective member should enclose the interface between the conductor 30 to the housing 22. In FIGS. 1, 5 and 6, an exemplary interface between the conductor 30 and the housing 22 is provided as a crimp connection 34. The protective member 50 of FIG. 5A and of FIG. 5B can be connected to the housing 22 using medical grade adhesive. Preferably, the medical grade adhesive is applied onto the entire outer perimeter of the protective member 50 and is also used to fill the entire area enclosed within the protective member.

The protective member 50 may be positioned a number of ways with respect to the housing 22. Factors which influence the positioning of the protective member with respect to the housing include, but are not limited to, the location and depth of the tissue site at which the device 10' is implanted.

The protective member 50 should be connected to the housing 22 via an appropriate adhesive. The adhesive should be effective to ensure the integrity of the connection between the protective member 50 and the housing 22 while the device 10' is implanted. The adhesive may also be used as a potting material to fill any gaps or pockets within the protective member 50. Acceptable adhesive materials will be known to the skilled artisan, however, one particular example is a medial grade adhesive.

FIGS. 5A, 5B and 6 also show a securing mechanism 60 which is effective to ensure that the device 10' remains secured to particular tissue site. One exemplary securing mechanism 60, as best shown in FIG. 6, is a tie-down mechanism, which allows for the housing 22 of the device 10' to be connected, for example by suturing, to a tissue site 61. The exemplary tie-down mechanism includes three lobes 62 which lie approximately 120° apart from each other, wherein each lobe generally has at least one suture site 64. One of ordinary skill in the art will realize that the number of lobes 62, and/or the number of suture sites 64 may be greater or lesser than the numbers that are described above and/or that are depicted in FIG. 6, and that each lobe 62 may be separated from the other lobes by an angle measurement greater or less than 120°.

As shown in exemplary FIG. 6, the suture sites 64 should be sized and placed in order to allow for one end of a suture thread 65 to be connected to the tissue site 61 through the securing mechanism 60 at each lobe 62. One of ordinary skill in the art will realize that each lobe 62 can have greater or less than one suture site 64, and a suture thread 65 does not necessarily have to be connected to the tissue site 61 at each suture site 64.

Those skilled in the art will recognize, or be able to ascertain using no more than routine experimentation, numerous equivalents to the specific procedures described herein. Such equivalents are considered to be within the scope of this invention and are covered by the following claims.

The contents of all references and patent applications described herein are hereby incorporated by reference.

What is claimed is:

1. An implantable electro-acupuncture device, comprising:
    an elongate, flexible conductor for applying an electric charge to a predetermined tissue locus, the conductor having a proximal end and a distal portion, the distal portion having a distal tip;
    a housing secured to the proximal end of the conductor; and
    an electrical source for providing an electric current to the conductor, the electrical source being disposed within the housing and in electrical connection with the conductor.

2. The implantable electro-acupuncture device of claim 1, wherein the conductor comprises at least one wire.

3. The implantable electro-acupuncture device of claim 1, wherein the device further comprises an insulator surrounding at least a portion of the conductor.

4. The implantable electro-acupuncture device of claim 3, wherein the conductor is electrically insulated from the housing.

5. The implantable electro-acupuncture device of claim 4, wherein the conductor is coated with an insulating layer, and wherein at least a portion of the distal tip is exposed though the insulating layer.

6. The implantable electro-acupuncture device of claim 1, wherein the electrical source comprises a receiver for receiving external signals, and a converter for converting the external signals to electrical impulses to supply electric current to the conductor.

7. The implantable electro-acupuncture device of claims 6, wherein converter comprises at least one inductive coil.

8. The implantable electro-acupuncture device of claim 6, wherein the signals are effective to control at least one variable with respect to the electrical impulses.

9. The implantable electro-acupuncture device of claim 8, wherein the at least one variable is selected from the group consisting of pulse width, pulse sequence, pulse interval and pulse power.

10. The implantable electro-acupuncture device of claim 1, wherein the conductor is an electrically conducting cable.

11. The implantable electro-acupuncture device of claim 10, wherein the cable is comprised of a plurality of flexible, multi-stranded cable bundles.

12. The implantable electro-acupuncture device of claim 1, wherein the housing is secured to the proximal end of the conductor via a connection element.

13. The implantable electro-acupuncture device of claim 12, wherein the connection element is a crimp connector.

14. The implantable electro-acupuncture device of claim 12, further comprising a protective member connected to the housing such that the protective member encloses the connection element.

15. The implantable electro-acupuncture device of claim 14, wherein the protective member is a strain relief boot.

16. The implantable electro-acupuncture device of claim 14, wherein the protective member is made of a biocompatible material.

17. The implantable electro-acupuncture device of claim 16, wherein the biocompatible material is an insulating material.

18. The implantable electro-acupuncture device of claim 17, wherein the material is selected from the group consisting of silicone and polyurethane.

19. The implantable electro-acupuncture device of claim 1, further comprising a securing member, the securing member being positioned between the housing and the tissue locus and being effective to secure the housing to the tissue locus, the securing member comprising:
    a plurality of lobes, wherein a cavity is defined in each lobe to form a plurality of suture sites, and wherein a plurality of suture threads secure the housing to the tissue site, a first end of each suture thread being sutured to the tissue site at each suture site and a second end of each suture thread being sutured to the housing.

20. The implantable electro-acupuncture device of claim 1, further comprising:
    an anchor disposed on the conductor, the anchor being effective to fix the conductor at the predetermined tissue locus to substantially inhibit movement of the conductor relative to the predetermined tissue locus.

21. The implantable electro-acupuncture device of claim 20, wherein the anchor comprises at least one fixation ring disposed about the conductor.

22. The implantable electro-acupuncture device of claim 20, wherein the anchor comprises a helical tissue-engaging member disposed at the distal portion of the conductor.

23. The implantable electro-acupuncture device of claim 1, wherein the housing comprises a fluid-tight enclosure.

24. The implantable electro-acupuncture device of claim 23, wherein the housing is hermetically sealed.

25. The device of claim 23, wherein the housing comprises an upper housing portion and a lower housing portion, the upper and lower housing portions being secured together in a fluid-tight relation, and wherein the lower housing portion is also secured to the conductor.

26. The device of claim 25, wherein the upper housing portion is secured to the lower housing portion by welding.

27. The device of claim 25, wherein the lower housing portion comprises a feedthrough effective to provide electrical continuity between the conductor and the electrical source.

* * * * *